United States Patent [19]

Scanlon

[11] Patent Number: 5,181,910
[45] Date of Patent: Jan. 26, 1993

[54] METHOD AND APPARATUS FOR A FLUID INFUSION SYSTEM WITH LINEARIZED FLOW RATE CHANGE

[75] Inventor: David A. Scanlon, Minneapolis, Minn.

[73] Assignee: Pharmacia Deltec, Inc., St. Paul, Minn.

[21] Appl. No.: 662,265

[22] Filed: Feb. 28, 1991

[51] Int. Cl.⁵ .......................................... A61M 37/00
[52] U.S. Cl. ..................................... 604/67; 604/65; 604/151; 128/DIG. 12
[58] Field of Search ................... 604/65, 67, 151–153; 128/DIG. 12, DIG. 13

[56] References Cited

U.S. PATENT DOCUMENTS

| | | | |
|---|---|---|---|
| 4,270,532 | 6/1981 | Franetzki | 604/151 |
| 4,624,661 | 11/1986 | Arimond | 604/151 |
| 4,685,903 | 8/1987 | Cable et al. | 604/151 |
| 4,692,145 | 9/1987 | Weyant | 604/65 |
| 4,785,799 | 11/1988 | Schoon et al. | 128/DIG. 12 |
| 5,010,473 | 4/1991 | Jacobs | 604/65 |

Primary Examiner—Stephen C. Pellegrino
Assistant Examiner—Ralph A. Lewis
Attorney, Agent, or Firm—Merchant, Gould, Smith, Edell, Welter and Schmidt

[57] ABSTRACT

A programmable infusion pump and controller for automatically determining the interval between pump activations necessary to produce a substantially linear rate of increase or decrease in fluid flow, during the administration of fluids to a patient. The infusion pump contains a user interface, with a keyboard to enter infusion volume, infusion period, and taper period. When the pump is turned on, the previous infusion parameters are retrieved from non-volatile memory. If the user attempts to alter the infusion parameters so as to violate the "rate too high" or "rate too low" criteria of the system, an alarm sounds and the user interface displays the "next best answer" possible. The pump also allows the user to initiate the taper sequence at any time during plateau or continuous fluid delivery.

10 Claims, 7 Drawing Sheets

METHOD AND APPARATUS FOR A FLUID INFUSION SYSTEM WITH LINEARIZED FLOW RATE CHANGE

BACKGROUND OF THE INVENTION

The present invention relates to a fluid infusion system which provides program delivery of intravenous fluids at a continuous flow rate or in a substantially linearized rate of increase or decrease.

Some medical conditions disrupt the normal processes by which the human body extracts nutrition from food, requiring intravenous administration of large quantities of hypertonic dextrose. This procedure is known as total parenteral nutrition or TPN.

The infusion of fluids into the human body is usually accomplished by means of administration set in conjunction with a metering apparatus which controls the flow rate of fluid through the set. Peristaltic-type pumps, which function by repetitively compressing an expanding a section of tubing, have proven particularly attractive for use in metering apparatus since they do not introduce the possibility of leaks or contamination into the system, while providing positive flow of fluid through the system.

In applications where medication is being administered, it is necessary to operate the peristaltic pump to infuse only a predetermined volume of fluid at a predetermined rate. Patients need a control system for peristaltic-type infusion pumps which enable them to preset a quantity of fluid and the rate of infusion. The system must continuously monitor the performance of the pump to insure compliance with the preset parameters and alert the operator in the event of a malfunction.

Because of the physiological effects associated with the sudden infusions of fluid into the human body, it is often desirable to gradually increase and decrease the rate at which the infusion system delivers the fluid. Rather than initiating the pump at the full rate of delivery, it is preferable that the system ramps or tapers up to the full delivery rate. Likewise, it is often desireable that the system gradually tapers down the delivery rate at the end of the cycle, rather than abruptly stopping fluid delivery.

This is particularly critical when the fluid being infused contains high concentrations of glucose. A sudden infusion of glucose directly into the blood stream can create substantial adverse effects on the patient, including disorientation and unconsciousness. Similar effects can also occur if the delivery rate is suddenly decreased.

A major problem with existing peristaltic-type pumps is that the resulting delivery of fluid occurs in a series of pulses or surges, the frequency of which is equal to the frequency of the passage of successive rollers in contact with the delivery tube. The effect is that fluid is delivered at widely varying rates during a pump cycle, which is unacceptable where uniformity of delivery rate is required.

The pulses or surges of fluid usually produced by peristaltic-type pumps are difficult to accurately convert into linear rates of increase or decrease. Use of a programmable infusion pump with taper-on and taper-off capabilities is discussed in U.S. Pat. No. 4,785,799, issued to Schoon et al. Schoon discloses a taper function with the number of steps dependent on an arbitrarily chosen increment of 5 ml/hr. The number of steps depends on the difference between the starting rate and the steady-state rate.

Programming of ambulatory infusion systems can be a complicated process. The average patient finds it difficult to calculate the appropriate infusion rate and period. This calculation is made extremely more complicated when tapers are involved. With most medical infusion pumps currently available, if the user attempts to program an infusion cycle that exceeds the minimum or maximum flow rate of the pump, an error message is given and the user is forced to recalculate the infusion parameters, rather than having the system suggest a valid parameter value.

Patient operated infusion systems also require a back-up capability which retains system parameters, even if power is lost. However, non-volatile memory devices have a limited useful life, which degrades in proportion to the number of write-sequences executed. This problem is further complicated by the fact that the amount of information necessary to back-up during a taper cycle is significantly greater then during continuous or plateau fluid delivery.

Finally, it is often desireable to retain previously programmed delivery cycles. However, pre-set infusion cycles should not interfere with the patients ability to "customize" the cycle. Specifically, a new delivery cycle should begin if any of the infusion parameters are changed and the patient needs the option to initiate the taper up or down sequence at any time during "plateau" or continuous fluid delivery.

SUMMARY OF THE INVENTION

The present invention relates to an ambulatory infusion system which utilizes the pulses or surges of fluid, which occur with peristaltic-type pumps, to create a substantially linearized rate of increase and decrease of fluid flow at the beginning and/or end of the delivery cycle.

An example of a device with the above capabilities is the CADD-TPN, Model 5700 ambulatory infusion, system, produced by Pharmacia Deltec of St. Paul, Minn.

The present invention is a control system for an ambulatory infusion pump to administer fluid to a patient. The system receives data corresponding to the total volume of fluid to be administered, the time period over which the fluid is to be administered, and the taper up and taper down infusion periods over which the fluid administration rate is to be linearly increased or decreased. The control system determines the interval between pump activations necessary to produce a substantially linear rate of increase or decrease in fluid flow, while ensuring that the total volume of fluid is administered within the desired infusion period. A pump control means activates the pump in accordance with the linear rate of increase or decrease calculated for the taper up and taper down sequence.

The invention also provides control means which calculate the interval between pump activations in a manner that greatly reduces rounding error inherent in microprocessor based calculations. Because the pump parameters are factored-up to integer-based unit system, some rounding errors are avoided.

The infusion controller provides pump control means which execute various infusion programs stored in memory, corresponding to a predetermined cycle. The infusion volume data and infusion period data are automatically converted into signals to drive the pump operation. The pump control performs the infusion cycle in accordance with parameters entered by the user.

Because of the unique linearization routine of the present invention, a pump calibration factor can be stored in the infusion controller for each individual peristaltic-type pump, thereby further enhancing the accuracy of the system.

The system monitors and retains the taper parameters in the event that power is temporarily lost. Upon return of power, the infusion cycle will be advanced by the maximum number of pump activations that could have occurred before the power was lost. The reset protocol begins a new delivery cycle if any of the delivery parameters are changed.

In order to simplify programming, the infusion parameters are programmed in a predetermined sequence. As each parameter is programmed, the system automatically constrains the allowable values for the subsequent parameters, thereby narrowing the range of possible values the patient may enter.

If the delivery cycle is paused and restarted, delivery begins at the location in the cycle when the pause command was initiated. Finally, if the delivery cycle is stopped during "plateau" or continuous fluid delivery, the user has the option to initiate the taper down sequence, avoiding the negative effects associated with the abrupt termination of infusion.

DETAILED DESCRIPTION OF THE PREFERRED EMBODIMENT

The portable infusion system of the present invention is designed primarily for the precise injection of accurate amounts of medicinal fluids during ambulatory intervascular therapy (TPN). However, it is obvious that the present invention may also be used for various other purposes including, the precise feeding of non-ambulatory patients or the precise injection of fluids into animals. It should also be recognized that the present invention could be used with non-peristaltic pumps.

Figure 1:
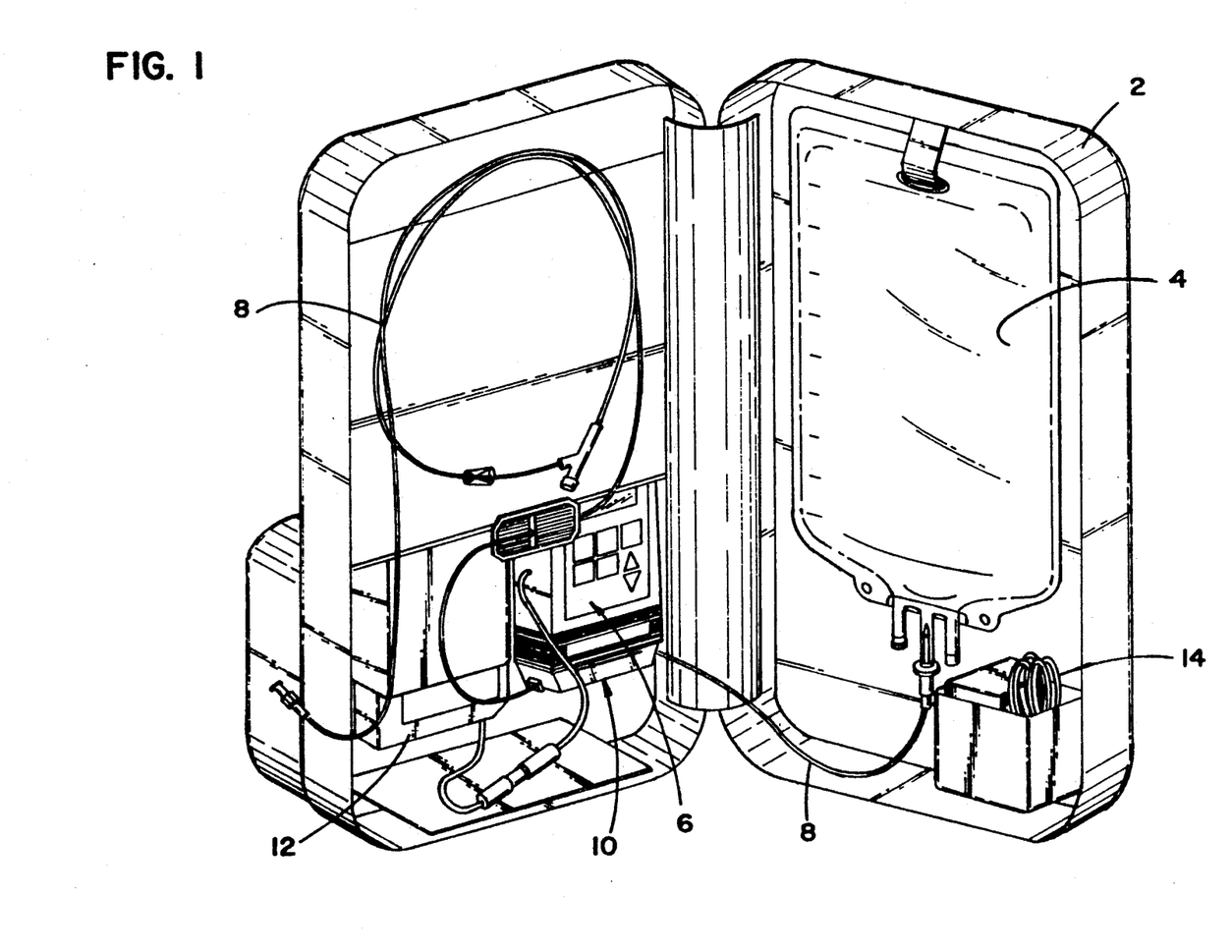
FIG. 1 is a perspective view of an ambulatory infusion system according to the present invention.
Figure 2:
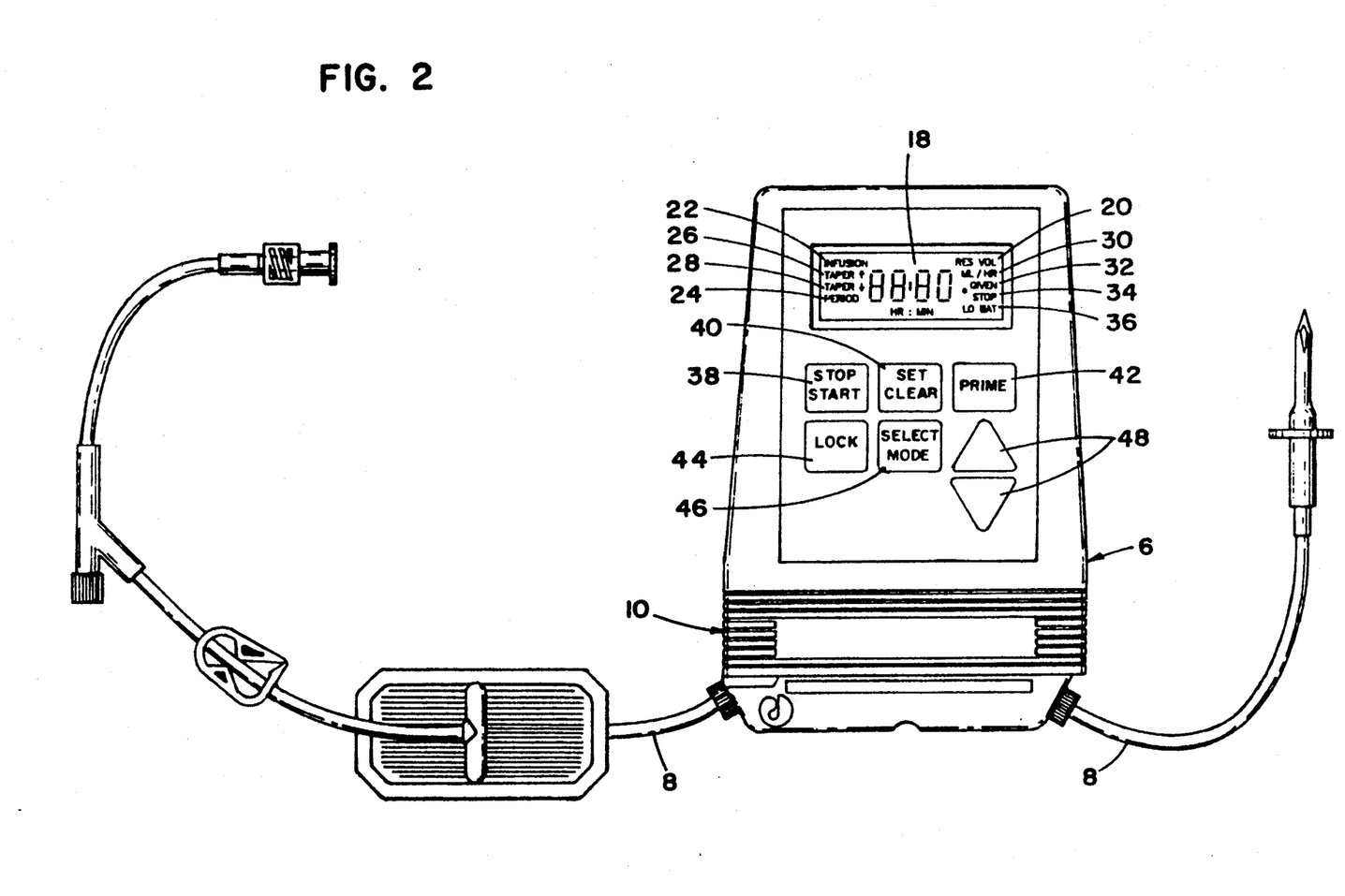
FIG. 2 is a front view of an infusion controller, along with the user interface and digital display.

Referring to FIGS. 1 and 2, the ambulatory infusion system comprises a carry case 2 containing a fluid container 4, and an infusion controller 6. The administration set 8 is preferably formed of a plastic material and packaged in a sterile condition. To avoid the danger of contamination, the administration set is normally utilized for one application only, and is disposed of after use.

The administration set 8 is connected to the fluid container 4 and passed through a groove in the bottom of the peristaltic-type pump 10. The pump is secured to the base of the infusion controller 6. The tubing of the administration set then continues out of the carry case, where it is attached to the patient.

A power pack 12 is provided to power the infusion system, as well as a AC adapter 14 for recharging the power pack or for non-ambulatory use of the system. The self-contained ambulatory infusion system of FIG. 1 is readily attached to the patient's body via a harness, (not shown) or as otherwise desired.

FIG. 2 illustrates the user interface 16 of the infusion controller. A liquid crystal digital display 18 is provided to indicate the pump's various control functions and the values programmed for the pump operation. These include the reservoir/residual volume (RES VOL) 20, infusion volume (INFUSION) 22, infusion period (PERIOD) 24, taper up period (TAPER ↑) 26, taper down period (TAPER ↓) 28, infusion rate (ML/HR) 30, and volume given in milliliters (GIVEN) 32. The digital display also indicates when the system is in the stop mode (STOP) 34 and when the power pack is low (LO BAT) 36.

The user interface includes a stop/start key (STOP/START) 38 which starts and stops the pumping cycle. The set/clear key (SET/CLEAR) 40 is used to enter new parameter values into the non-volatile memory or for clearing program values from memory. The prime key (PRIME) 42 is used to prime the fluid path and to remove air bubbles from the fluid path. The lock key (LOCK) 44 is used to restrict changes in the pump's operation and to illustrates the status of the different lock levels available in the controller. The select mode key (SELECT MODE) 46 is used to display the pump's programmed values. The scroll keys 48 are used to increase and decrease program values, which will appear in the pump's display.

Figure 3:
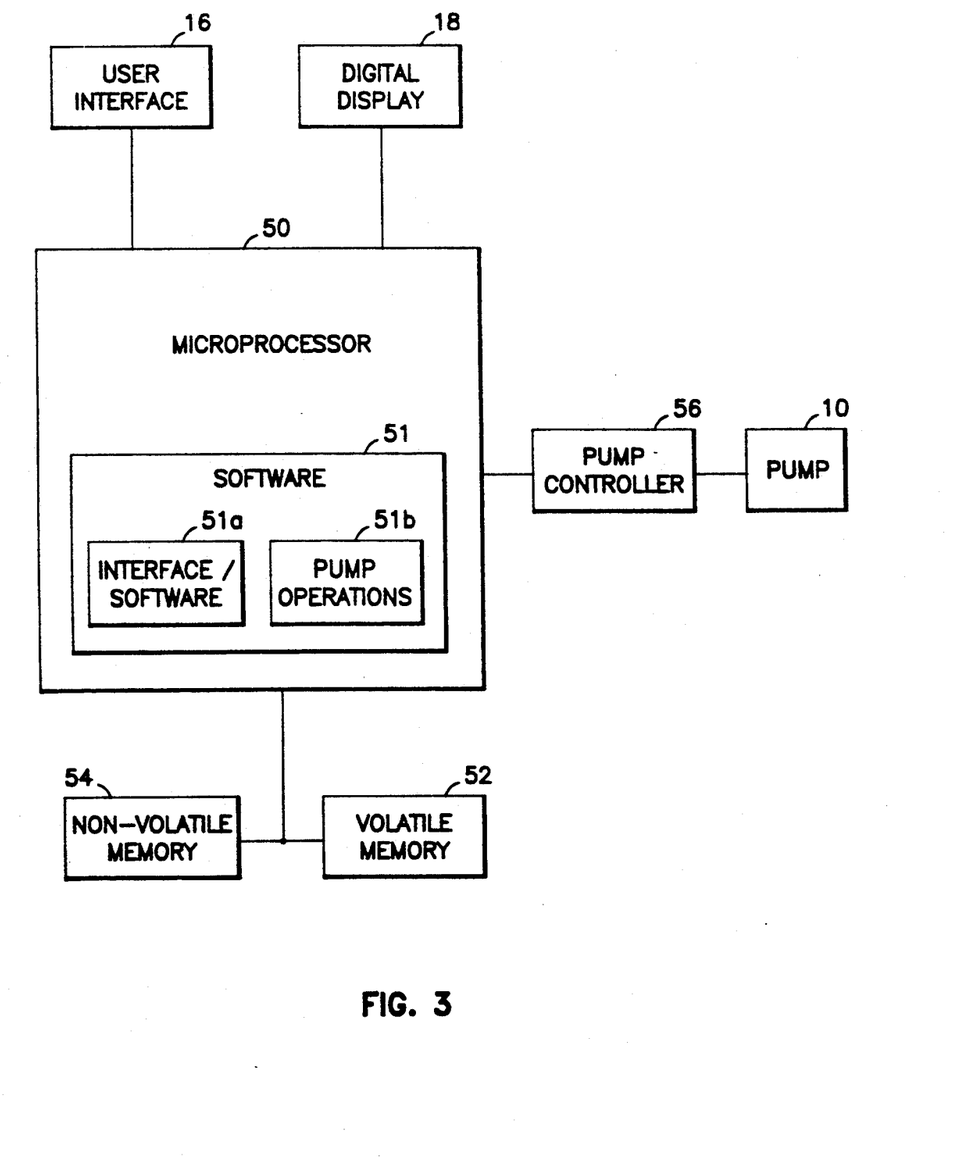
FIG. 3 is a simplified block diagram of the infusion pump controller hardware and software of the present invention.

As illustrated in FIG. 3, the user interface 16 and the digital display 18 of the infusion controller 6 are connected to a microprocessor 50. The microprocessor communicates with volatile memory 52 and non-volatile memory 54 and executes and operates according to software 51, which may be stored in the non-volatile memory 54 or in another suitable permanent memory device as desired. When the microprocessor 50 determines that the pump is to be activated, a signal is sent from the microprocessor to the pump controller 56, which activates the pump 10.

Figure 4A:
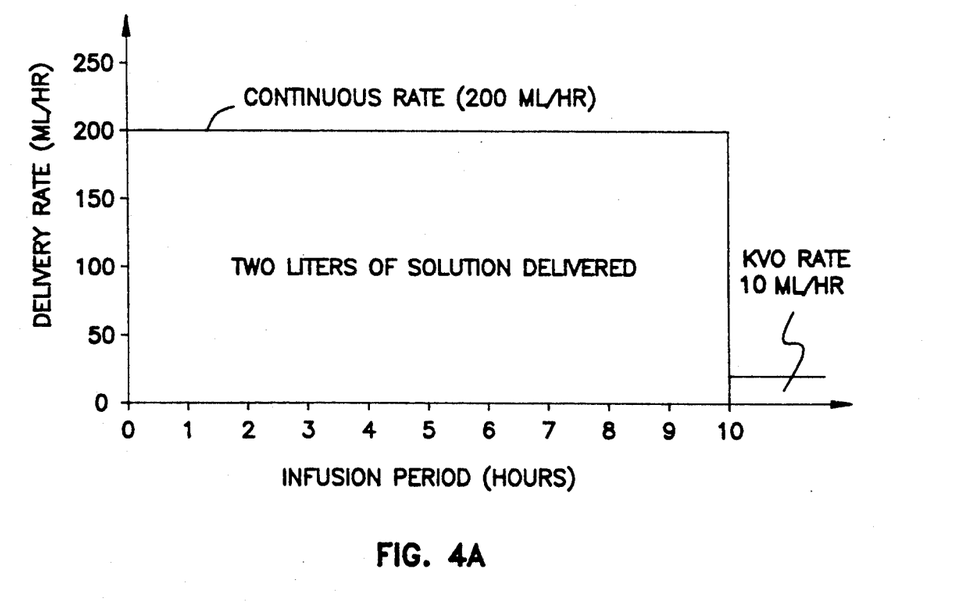
FIGS. 4A and 4B are time-rate diagrams of a sample fluid delivery cycle.

Under the control of software 51, the pump can deliver solutions at a continuous infusion rate without any tapering at the beginning or end of the cycle, as illustrated in FIG. 4A. For example, two liters of solution are delivered during a 10-hour infusion period at a continuous infusion rate of 200 milliliters per hour. The area under the delivery curve in FIG. 4A represents the total fluid delivered during the infusion cycle. (200 ml/hr × 10 hrs = 2000 ml = 2 liters).

As will be described further below, the pump can also be programmed to taper up or taper down the infusion rate at the beginning or end of the programmed infusion period. The taper up and taper down sequences can be made to occur over a short or a long period, depending on how the pump is programmed.

Figure 4B:
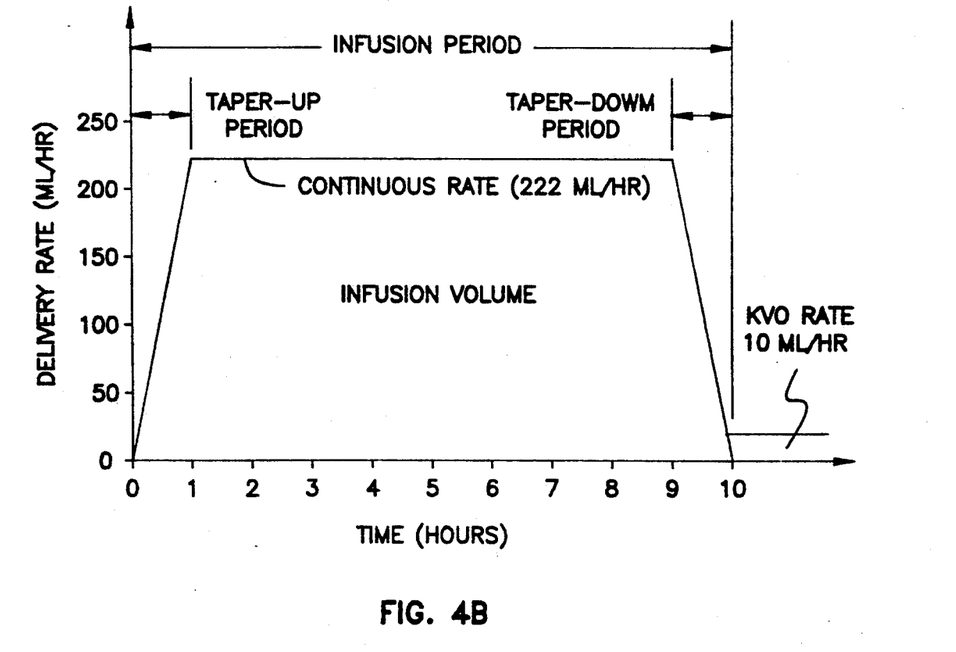

An example of tapering the delivery of two liters of fluid, over a 10-hour infusion period, is illustrated in FIG. 4B. The pump slowly increases the infusion rate in the first hour of infusion. Between the second and ninth hours of infusion, the solution is delivered at a continuous rate of 222 milliliters per hour. In the last hour, the infusion rate decreases to the KVO rate.

The example of FIG. 4B corresponds to the same infusion parameters as in FIG. 4A. Specifically, two liters of solution are delivered over a 10-hour period. It is important to note that the continuous rate or "plateau rate" is higher in FIG. 4B in order to compensate for the reduced infusion rates during the taper up and taper down periods.

At the end of all infusion cycles, the rate of infusion automatically switches to 10 milliliters per hour, as illustrated in FIGS. 4A and 4B. This rate is referred to as the KVO (keep vein open) infusion rate. It permits a minimal amount of solution to flow after the regular infusion volume has been delivered, to prevent the vein from collapsing. It should be noted that the KVO rate can be set at a value other then 10 ml/hr in alternate embodiments of the present invention, depending on a number of medically related factors. The above described pumping functions are accomplished under the control of software 51, which operates within the infusion controller to control the pump 10.

Under the control of software 51, the microprocessor 50 monitors the amount of fluid infused, and automatically calculates and communicates to display 18 the quantity of fluid remaining in the fluid container, in milliliters. When the reservoir/residual volume decreases to 50 milliliters, a short alarm sounds to notify the user. With each subsequent 10 milliliter decrease of the reservoir volume, another alarm sounds. When the reservoir volume reaches 0 milliliters, a continuous alarm will indicate that the fluid container is empty and the pump 10 will stop automatically, terminating the KVO delivery.

Figure 5:
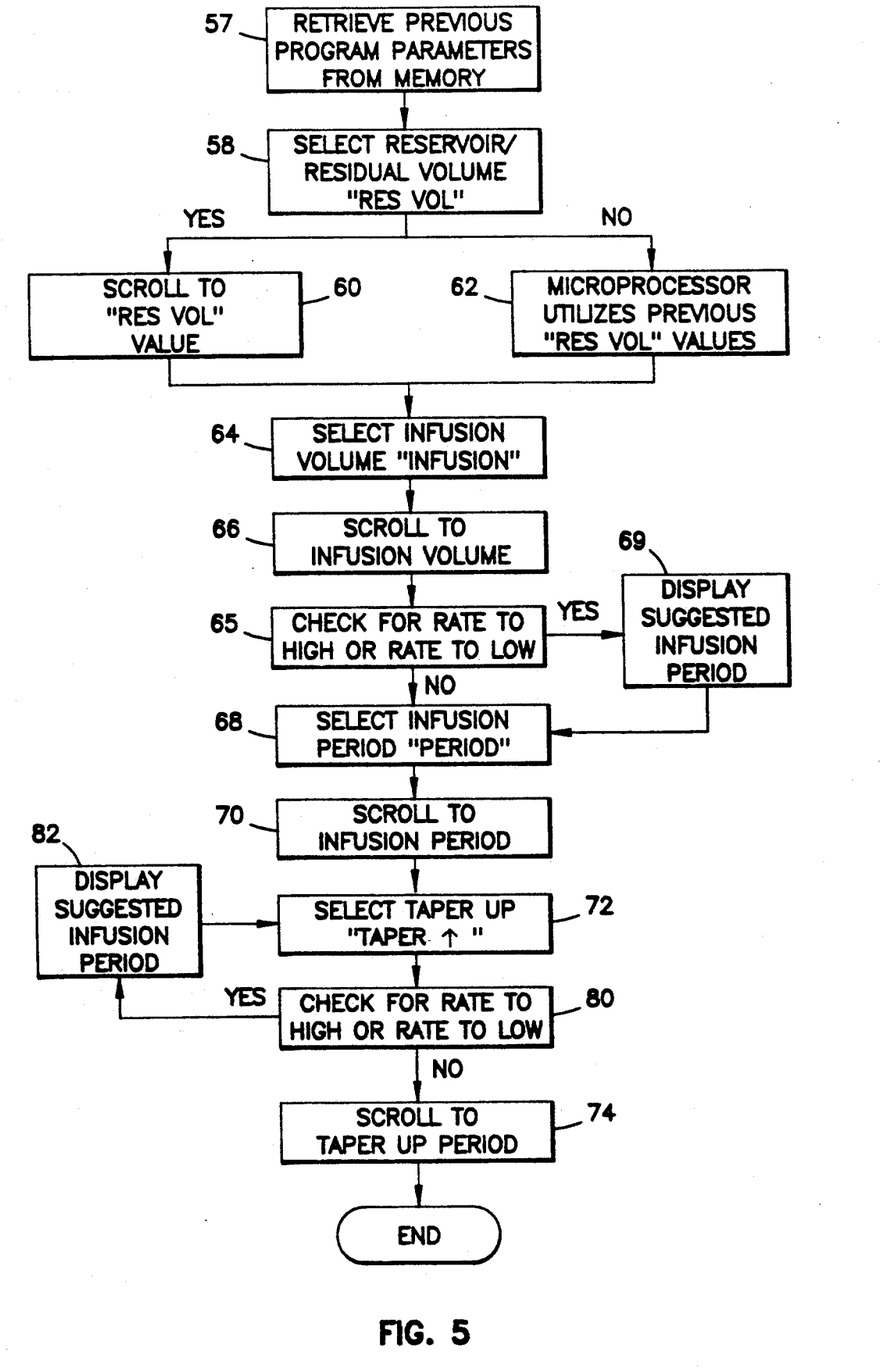
FIG. 5 is a flow chart for programming the infusion controller.

In order to simplify the programming of the pump, the user interface 16 accepts infusion parameters in a predesignated priority sequence. FIG. 5 comprises a flow chart corresponding to the programming steps of the infusion controller. The flow chart also generally corresponds to the operation of software 51 to control microprocessor 50 and infusion controller 6.

When the pump is activated, the previous program parameters are retrieved from the non-volatile memory 57. As each parameter mode is entered, either the retrieved parameters are displayed or the system calculates the "next best answer" permissible for a given infusion volume.

The next best answer feature operates in conjunction with the programming parameter priority, discussed below. The purpose of the next best answer function is to direct the user to an acceptable infusion parameter, with the smallest number of iterations. Once the infusion volume is entered, the system either displays the previous infusion period or if the software 51 determines a rate to high or rate to low condition exist, the "next best answer" is displayed.

To enter the reservoir/residual volume the user merely presses the select mode key until the "RES VOL" appears in the display 58. By pressing the scroll keys, the user can select the quantity of fluid 60 in the fluid container. Pressing the set/clear key 40 cause the reservoir/residual volume to be entered into the non-volatile memory. If the user chooses not to enter a new RES VOL value, the previously programmed RES VOL value will be utilized by the microprocessor 62, retrieved in step 57 from the non-volatile memory.

The infusion volume 22 is the volume of solution that is programmed to be delivered to the patient. The user presses the select mode key until "INFUSION" appears in the display 64, and the infusion volume retrieve from memory is displayed. The infusion volume can be changed by pressing the scroll keys until the desired value is displayed 66. Pressing the set/clear key 40 causes the infusion volume to be entered into the non-volatile memory and the user continues to the next parameter.

Next, the software 51 checks for rate to high or rate to low 65, based on the infusion volume entered and the infusion period previously retrieve from memory. A "rate too high" or a "rate too low" alarm will be generated by programming module 51a if the values violate program limitations. These alarms are triggered if the mechanical rate of the pump required to deliver the desired infusion volume is exceeded, or if the programmed rate drops below 2 times the KVO rate. The software 51 responds to a rate to high or rate to low alarm by displaying a permissible infusion period (i.e., "the next best answer") 69 for the infusion volume previously entered.

At this point, the user then has the option selecting the displayed infusion period 68 by pressing the set/clear key or scrolling to another infusion period 70, constrained by the minimum allowable period calculated by the infusion controller. Again, pressing set/clear key 40 cause the selected infusion period to be entered into the non-volatile memory. As previously indicated, the above functions of the infusion controller 6 are done under the control of software 51, and in particular module 51a, which controls the programming functions.

The taper up period is the total amount of time, at the beginning of the infusion cycle, when the infusion rate is gradually increased in a linear fashion, until it reaches the continuous rate. The user presses the select mode key until the taper up appears 72 in the display. The software 51a again checks if the taper period is either too high or too low for the current infusion volume 80. A "rate too high" or a "rate too low" alarm is generated by programming module 51a if the value current value violates program limitations. If the pumping capacity of the system is exceeded, the program module 51a calculates the "next best answer" and displays it 82 for the user. Otherwise, the previous taper is displayed.

The scroll keys are used to change the taper up period 74, constrained by the previously entered program parameters. Specifically, the system prevents the user from entering tapers that violate the rate to high or rate to low constraints. The set/clear key cause the taper period to be entered into the non-volatile memory. A similar procedure is followed to set the taper down period. (Not shown). The system allows for either a taper up or taper down period, or both. The length of the taper periods are likewise independently programmed. At this point, the start key is pressed to initiate the infusion cycle.

Additionally, the infusion controller includes a pause mode, which is controlled by the software 51. If the pump is put in the pause mode during the infusion cycle and then restarted, the program module 51a will retrieve the program parameters from the non-volatile memory, and the pump is restarted at the point in the infusion cycle where it left off. Because the program parameters are stored in non-volatile memory, the system keeps track of where it is in the infusion cycle.

It may be necessary for medical reasons to stop infusion during delivery, via the stop/start key 38. If the system is stopped, the user has the option to initiate the taper down sequence immediately. If immediate taper down is requested, the pump operation software 51b initiates the taper sequence. This feature allows the user to initiate a taper down sequence at any time during the continuous or plateau delivery cycle.

The non-volatile memory device 54 used to store system parameters has a limited life, which degrades as the number of "write" operations executed increases. Because of this limitation, the system back up functions, contained in program module 51a, are designed to minimize the number of write operations to the memory device.

When the system is operating in a continuous or plateau rate, only the number of activations remaining and the time remaining in the delivery cycle are stored in the non-volatile memory. However, during the taper sequence, significantly more information needs to be recorded in order to retain the exact location in the infusion cycle.

Early in the taper up cycle, there are a few pump strokes per unit time. Therefore, the write sequences to the non-volatile memory are performed on a timed basis. Later in the taper up cycle, the number of pump activations per unit time increase significantly. Therefore, the write sequence to the non-volatile memory is triggered by a specific number of pump activations. As a general rule, the present embodiment of the system attempts to record the status of the system parameters every 40 pump activations or every 4 minutes, which ever comes first. The above description is obviously reversed when analyzing the taper down sequence.

In the event the battery is removed and subsequently replaced during an infusion cycle, the non-volatile memory device will not contain an exact summary of the back up parameters. In this event, when the infusion cycle is restarted the software 51 extrapolates how far into the infusion cycle it could have been, based on a known predetermined maximum amount of time or total activations between updates, had the battery not been removed.

The purpose of this extrapolation is to calculate the greatest quantity of fluid that could have been infused to the patient. The system is designed to "under-deliver" fluids, rather than risking adverse effects from "over-delivery".

Taper Rate Linearization Function

As discussed above, peristaltic-type infusion pumps propel a discrete quantity of fluid in response to each pump activation. Consequently, the flow rate of such pumps can be changed only by varying the interval between pump activations. For example, by reducing the interval between pump activations, a greater flow rate per unit time can be achieved.

The taper rate linearization function of the present invention is designed to determine the interval between pump activations necessary to produce a substantially linear rate of increase or decrease in the fluid flow. The taper periods, as illustrated in FIGURE 4B, define a triangular shape, with taper period on the horizontal axis and delivery rate on the vertical axis. The area under the taper curve represents the total volume of fluid delivered during the taper cycle. The taper rate linearization function, which is a software routine of pump operations software 51b, begins by dividing the taper period by 256 and the plateau delivery rate by 256. The result is a substantially linearized taper comprised of 256 discrete steps.

The routine then determines the total volume in the taper cycle as well as the number of pump activations required during the taper. The volume under the taper curve corresponds to one-half of the rate of the plateau times the taper period (i.e., the area of the triangle). The number of pump activations required during a taper sequence is determined by dividing the total volume of fluid in the taper sequence by the fluid volume advanced per pump activation. The volume per pump activation is determined experimentally and a calibration factor is entered into the non-volatile memory of the infusion controller for each individual pump unit.

Figure 6:
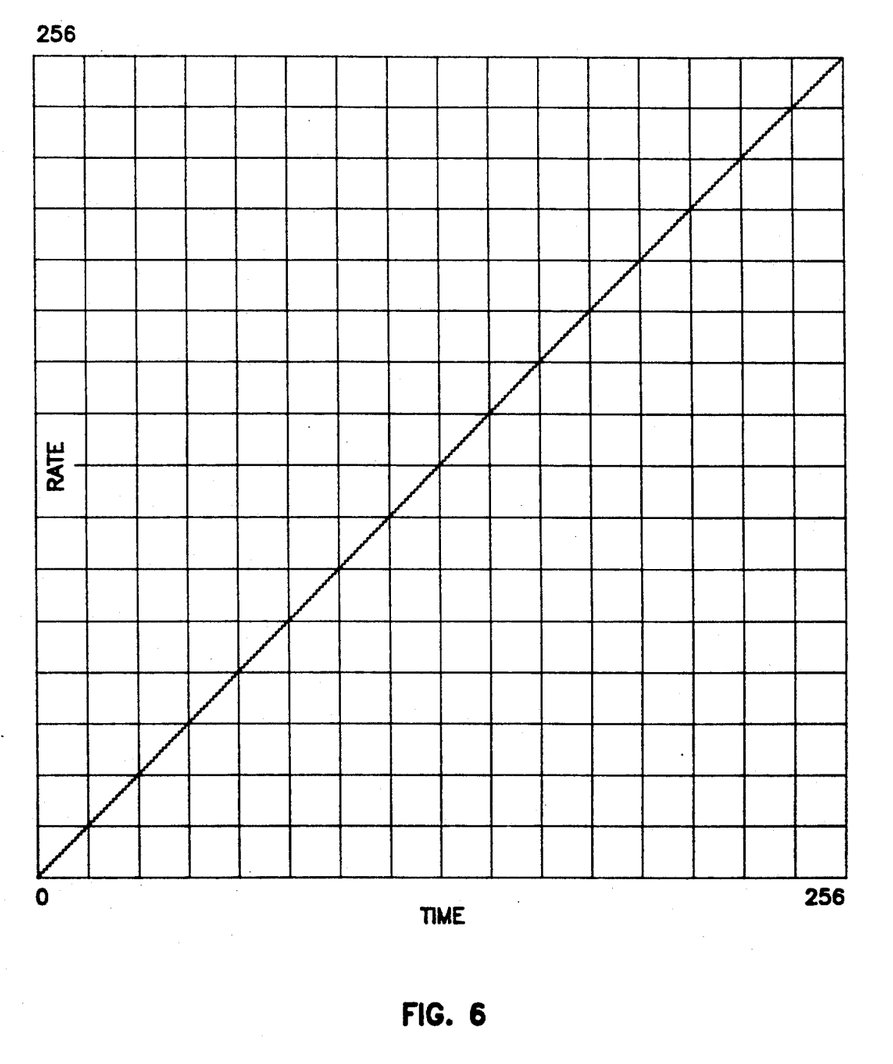
FIG. 6 is a time-rate diagram illustrating the manner in which the taper is divided into discrete steps.
Figure 7:
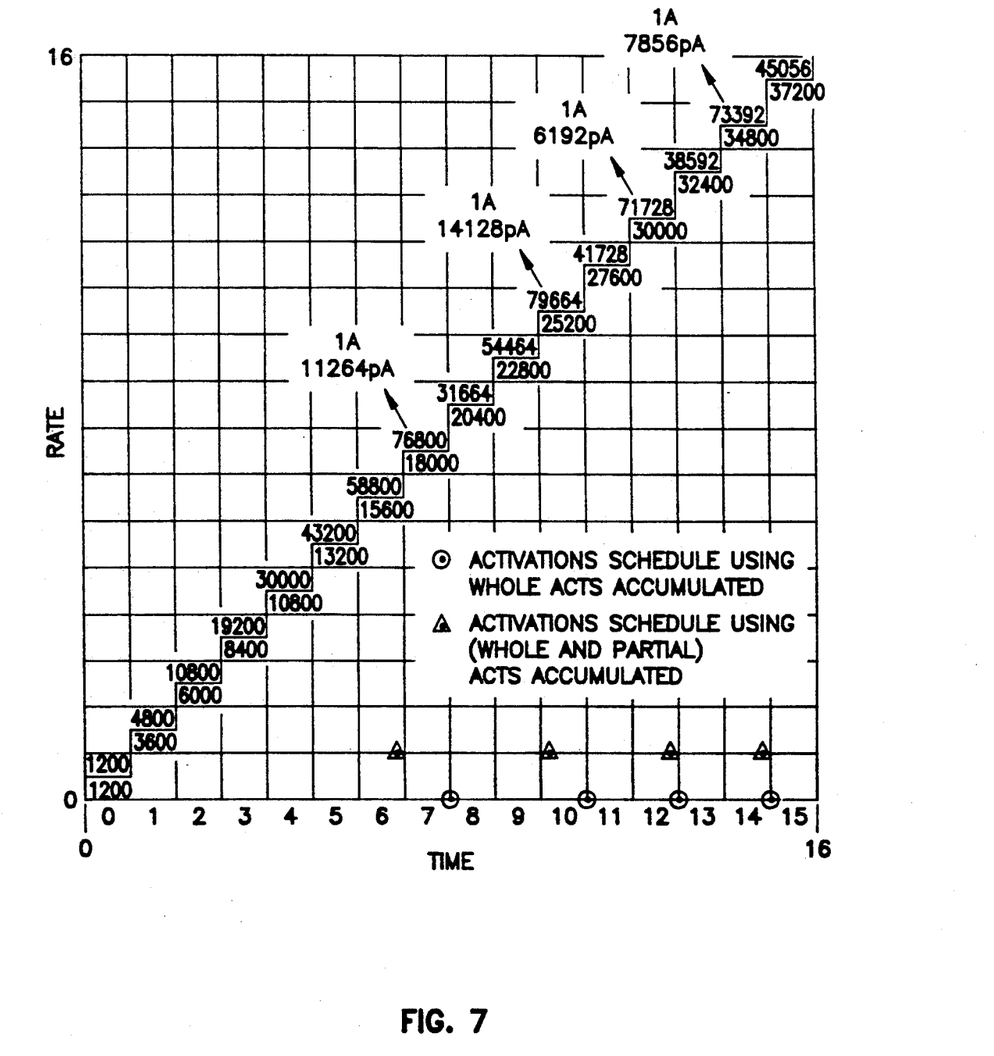
FIG. 7 is an example of the initial discrete steps associated with a specific example of a taper cycle, along with a sample calculation.

The area under the curve of the taper illustrated in FIG. 6 is 256 time increments and 256 incremental increases in the delivery rate, corresponds to 32,768 squares. Half height squares—rectangles—were chosen so that the area above and below the taper line of FIG. 6 are mirror images of equal area, where the first and last steps are a half square. (There are 65,536 rectangles or half-squares ($2 \times 32,768$) under the taper curve). FIG. 7 illustrates that the first step is a half square.

The example of FIG. 7 illustrates the first 16 time zones of a 180 minute taper period, with a plateau rate of 200 ml/hr (3.33 ml/minute). The volume under the taper curve is $\frac{1}{2}$ (plateau rate $\times$ taper period) or ($\frac{1}{2}(200)(180/60))=300$ ml.

Next, the total number of pump activations required during the taper cycle is calculated by the routine, by dividing the total volume of fluid in the taper by the amount of fluid propelled during each pump activation. The pump operations software 51b retrieves the calibration factor for the pump from the non-volatile memory. In the present example, the calibration factor is 0.25 ml of fluid for each pump activation. (300 ml)/(0.25 ml/activation)=1200 pump activation during the taper sequence.

The routine defines 65,536 partial activations as one actual pump activation. By dividing the total number of pump activations during the taper sequence by the number of rectangles under the curve (65,536), and multiplying the result by the number of partial activations in one pump activation (65,536) a new unit of measure is defined, wherein each rectangle represents a discrete number of partial pump activations.

The units were chosen such that the quantity of partial acts is represented by whole number. This factoring-up of the units of measure minimizes rounding errors, which often occur during microprocessor based division operation.

As seen in FIG. 7, the first half step represents 1200 partial acts, where 2400 partial acts equals one step. The next step equals 3600 partial acts (1200+2400) plus the previous 1200 partial acts, totaling 4800 partial acts.

The routine continues to sequentially sum up the number of partial activations over time on a step-by-step basis, until 65,536 partial activations is equaled or exceeded, at which time the pump is again activated. (see step 7 of FIG. 7). The time period necessary to reach the next step, where the total partial acts equals or exceed 65,536 partial activations, equals or exceeds the time interval until the next pump activation.

However, as is clear from FIG. 7, the summation of partial pump activations at any given step will seldom exactly equal 65,536 partial acts, the number of partial act per pump activation. Consequently, when more than 65,536 partial activations is reached, the routine must subtracts 65,536 from the total number of partial activations for that particular step and carries the remainder forward to the next summation cycle.

It can be seen in FIG. 7 that the activation schedule based on reaching the next discrete step, whereby 65,536 partial activations is achieved or exceeded (whole acts accumulated), does not correspond to the theoretical time when 65,536 partial acts is actually reached. Rather, a step generally comprises 65,536 partial acts (one pump activation) plus some remaining number of partial activations. Therefore, the routine pro-rates back from the actual time to reach the step to a more precise, real-time location when the pump theoretically should be activated.

For example, step 7 in FIG. 7 represents one pump activation (65,536 partial acts) plus an excess of 11,264 partial acts, which are carried forward into the summation for the next pump activation. Step 7 also represents 8 time zones. (zone 0 through zone 7.) By dividing the total period of the taper sequence by 256 and multiplying the result by the 8 time zones, the number of minutes actually represented by the 8 zones can be calculated.

Next, the actual number of partial activations achieved at step 7 (76,800) is divided by the theoretical number of partial activations per pump activation, 65,536. This calculation produces a ratio greater than one, which represents one pump activation plus some number of remaining partial acts. By dividing the number of minutes represented by the 8 time zones by this ratio of actual vs. theoretical pump activations, the actual number of minutes —real-time—to the first pump activation can be calculated.

As seen in FIG. 7, the theoretical pump activation occurs some time in zone 6, when 65,536 partial activations was actually reached, as represented by the triangle. By pro-rating where the actual pump activation would occur back to its theoretical occurrence, the linearization function becomes significantly more accurate.

Thus, in summary, the linearization routine performs the following steps:

1. Dividing the taper period and plateau delivery rate by 256.
2. Calculating the total volume delivered during the delivery cycle.
3. Calculating the total number of pump activations necessary during the delivery cycle, utilizing a pump calibration factor.
4. Defining a theoretical pump activation as the number of half-squares under the taper curve.
5. Creating a new unit of measure by dividing the total number of pump activations during the taper sequence by the number of rectangles under the curve (65,536), and multiplying the result by the number of partial activations in one pump activation (65,536).
6. Sequentially sum up the number of partial activations over time on a step-by-step basis until 65,536 partial activations is reached or exceeded.
7. Pro-rating back the actual time necessary to reach the step to a theoretical step where 65,536 partial pump activations was reached.
8. Transmitting to the pump controller the time interval for the next pump activation.
9. Activating the pump.

The routine is designed to calculate the time interval until the next pump activation. After the pump is activated, the software 51b again starts summing up the number of partial activations on a step-by-step basis until 65,536 partial acts is reached or exceeded. The total of partial pump activations is again pro-rated to calculate the exact time interval until the next pump activation should occur. This process continues until the entire taper is pumped to the patient.

By defining 65,536 partial pump activations as a single pump activation, all calculations are performed on integers. This strategy greatly reduces the rounding error inherent in complex microprocessor based calculations.

While a particular embodiment has been described, it will be appreciated that modifications can be made without departing from the scope of the invention as defined by the appended claims.

I claim:

1. A programmable infusion pump for administering fluid to patients, comprising:

input means for receiving (i) the total volume of fluid to be administered to the patient during the infusion cycle, (ii) an infusion period over which the fluid is to be administered, and (iii) a taper infusion period over which the rate of fluid infusion is to change linearly;

pump means for administering a fixed volume of fluid to the patient per pump activation;

means for determining the variable time interval between pump activations necessary to produce a substantially linear rate of change of fluid flow during said taper infusion period constrained by said total volume of fluid to be administered during said infusion cycle, the means for determining said variable time interval between pump activations comprising;

a) means for determining the total number of pump activations required to deliver the volume of fluid scheduled for said taper infusion period;

b) means for dividing said taper infusion period into a plurality of steps, wherein each step corresponds to a variable quantity of fluid pumped per fixed time interval;

c) means for dividing each of said steps into a number of partial pump activations so that the number of partial pump activations per step is a whole number, thereby defining a new unit of measure where each pump activation corresponds to a whole number of partial pump activations;

d) means for sequentially totaling said plurality of partial pump activations on a step-by-step basis over said taper infusion period and determining the variable time intervals where said total number of partial activations equals or exceeds one complete pump activation, the means for sequentially totaling further including means for retaining the number of partial pump activations in excess of one complete pump activation and adding said number of partial pump activations in excess of one complete pump activation to the next total of partial pump activations in the sequence;

e) means for determining said variable time interval between pump activations according to when said total number of partial pump activations equals one complete pump activation; and pump control means for initiating said pump means in accordance with said variable time interval between pump activations to produce said substantially linear rate of change.

2. The programmable infusion pump of claim 1, wherein said taper infusion period is a taper-up cycle at the beginning of said infusion cycle.

3. The programmable infusion pump of claim 1, wherein said taper infusion period is a taper-down cycle at the end of said infusion cycle.

4. The programmable infusion pump of claim 1, further comprising means for utilizing a pump calibration factor unique to said pump means to determine the total number of pump activations required to deliver the volume of fluid scheduled for said taper infusion period.

5. The programmable infusion pump of claim 1, further comprising means for determining a plateau rate with a constant rate of fluid flow, and for controlling said pump means to deliver fluid at said plateau rate.

6. The programmable infusion pump of claim 1, wherein the means for dividing said taper infusion period into a plurality of steps divides said taper infusion period into n fixed time intervals and r incremental increases in the rate of fluid flow, where n is a power of two (2).

7. A method of administering fluid to a patient, comprising the steps of:
1) selecting the total volume of fluid to be administered to the patient during the infusion cycle;
2) selecting the infusion period over which the fluid is to be administered;
3) selecting a taper infusion period over which the rate of fluid infusion is to change linearly;
4) providing pump means for administering fluid to the patient;
5) determining the variable time interval between pump activations necessary to produce a substantially linear rate of change of fluid flow during said taper infusion period constrained by said total volume of fluid to be administered during said infusion cycle, comprising the steps of:
   a) determining the total number of pump activations required to deliver the volume of fluid scheduled for said taper infusion period;
   b) dividing said taper infusion period into a plurality of steps, wherein each step corresponds to a variable quantity of fluid pumped per fixed time interval;
   c) dividing each of said steps into a number of partial pump activations so that the number of partial pump activations per step is a whole number, thereby defining a new unit of measure where each pump activation corresponds to a whole number of partial pump activations;
   d) sequentially totaling said plurality of partial pump activations on a step-by-step basis over said taper infusion period and determining the variable time intervals where said total number of partial activations equals or exceeds one complete pump activation, the totaling step further including retaining the number of partial pump activations in excess of one complete pump activation and adding said number of partial pump activations in excess of one complete pump activation to the next total of partial pump activations in the sequence;
   e) determining said variable time interval between pump activations according to when said total number of partial pump activations equals one complete pump activation; and
6) activating said pump means in accordance with said time interval between pump activations to produce a substantially linear rate of change.

8. The method of claim 7, wherein said taper infusion period is a taper-up cycle at the beginning of said infusion cycle.

9. The method of claim 7, wherein said taper infusion period is a taper-down cycle at the end of said infusion cycle.

10. The method of claim 7, further comprising the step of utilizing a pump calibration factor unique to said pump means to determine the total number of pump activations required to deliver the fluid of said taper infusion period.

* * * * *